(12) United States Patent
Kwon et al.

(10) Patent No.: US 7,723,093 B2
(45) Date of Patent: May 25, 2010

(54) URACIL-DNA GLYCOSYLASE OF PSYCHROBACTER SP. HJ147 AND USE THEREOF

(75) Inventors: Suk-Tae Kwon, Suwon-si (KR); Mi-Sun Lee, Suwon-si (KR); Gun-A Kim, Anyang-si (KR); Jung-Hyun Lee, Seongnam-si (KR)

(73) Assignee: Sungkyunkwan University Foundation for Corporate Collaboration, Suwon, Gyeonggi-Do (KR)

( * ) Notice: Subject to any disclaimer, the term of this patent is extended or adjusted under 35 U.S.C. 154(b) by 204 days.

(21) Appl. No.: 11/823,123

(22) Filed: Jun. 26, 2007

(65) Prior Publication Data

US 2008/0299609 A1 Dec. 4, 2008

(30) Foreign Application Priority Data

Mar. 12, 2007 (KR) ...................... 10-2007-0023976

(51) Int. Cl.
*C12N 9/24* (2006.01)
*C12N 9/00* (2006.01)
*C12N 1/21* (2006.01)
*C12Q 1/68* (2006.01)
*C12P 21/06* (2006.01)
*C12N 15/70* (2006.01)
*C12P 19/34* (2006.01)
*C07H 21/04* (2006.01)

(52) U.S. Cl. ...................... 435/200; 435/183; 435/69.1; 435/252.33; 435/320.1; 435/91.2; 435/6; 536/23.2

(58) Field of Classification Search ........................ None
See application file for complete search history.

(56) References Cited

U.S. PATENT DOCUMENTS 7,273,730 B2 * 9/2007 Du Breuil Lastrucci .... 435/91.2

OTHER PUBLICATIONS

UniProt Accession No. Q4FRL3, Uracil-DNA glycosilase, created Aug. 30, 2005.*
Whisstock et al. Quaterly Reviews of Biophysics, 2003, "Prediction of protein function from protein sequence and structure", 36(3): 307-340.*
Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep 7, 1999;38(36):11643-50.*
Tomas Lindahl; "An N-Glycosidase from *Escherichia coli* That Releases Free Uracil from DNA Containing deaminated Cytosine Residues"; Proc. Nat. Acad., Sci. USA; vol. 71; No. 9; Sep. 1974; pp. 3649-3653.

Renxiang Chen, et al.; "Roles of uracil-DNA glycosylase and dUTPase in virus replication"; Journal of General Virology; vol. 83; (2002; pp. 2339-2345.
Olav Lanes, et al., "Identification, cloning, and expression of uracil-DNA glycosylase from Atlantic cod (*Gadus morhua*): characterization and homology modeling of the cold-active catalytic domain"; Extremophiles; (2002); 6; pp. 73-86.
H. Sobek, et al.; "Heat-labile uracil-DNA glycosylase: purification and characterization"; FEBS Letters 388; (1996); pp. 1-4.
Udaykumar, et al.; *A novel method emploiying UNG to avoid carry-over contamination in RNA-PCR*; Nucleric Acids Research; 1993; vol. 21, No. 16; pp. 3917-3918.
Edward W. Taggart, et al.; "*Use of heat labile UNG in an RT-PCR assay for enterovirus detection:*"; Journal of Virological Methods; 105; (2002); pp. 57-65.
Stephan Jaeger, et al.; Molecular cloning, sequencing, and expression of the heat-labile uracil-DNA glycosylase from a marine psychrophilic bacterium, strain BMTU3346:; Extremophiles; (2002); 4; pp. 115-122.
Alessandro A. Sartori, et al.; "*A novel uracil-DNA glycosylase with broad substrate specificity and an unusual active site*"; European Molecular Biology Organization; vol. 21; No. 12; (2002); pp. 3182-3191.
Naotake Ogasawara, et al.; "Systematic Sequencing of the 180 Kilobase Region of the *Bacillus subtilis* Chromosome Containing the Replication Origin"; DNA Research 1; (1994); pp. 1-14.
P. Secades, et al.; "Purification and properties of a new psychrophilic metalloprotease (Fpp2) in the fish pathogen *Flavobacterium psychrophilum*"; FEMS Microbiology Letters 226; (2003); pp. 273-279.
Moo Seok Seo, et al; "Cloning and expression of a DNA ligase from the hyperthermophilic archaeon *Staphylothermus marinus* and properties of the enzyme"; Journal of Biotechnology 128; (2007); pp. 519-530.
R. Cone, et al.; "Partial purification and characterization of a uracil DNA N-glycosidase from *Bacillus subtilis*"; Biochemistry; 1977 Jul, 12; 16(14):3194-3201.

(Continued)

*Primary Examiner*—Richard Hutson
*Assistant Examiner*—Iqbal H Chowdhury
(74) *Attorney, Agent, or Firm*—Edwards Angell Palmer & Dodge LLP; Kongsik Kim

(57) ABSTRACT

The present invention provides uracil-DNA glycosylase (UDG) gene originating from *Psychrobacter* sp. HJ147, and amino acid sequences deduced from the gene; expression and purification of Psp HJ147 UDG gene in *Escherichia coli*; and characterization of UDG obtained therefrom, and the use thereof in a polymerase chain reaction (PCR). The UDG according to the present invention has a specific activity of excising uracil bases in a uracil-containing DNA substrates at a low temperature, and is easily heat-inactivated. It thus can effectively eliminate cross contamination and carry-over contamination of PCR templates often occurring after a PCR process using dUTP. Therefore, it is useful for increasing preciseness (elimination of false positives), purity and amplification efficiency of PCR.

6 Claims, 8 Drawing Sheets

OTHER PUBLICATIONS

H. A. Erlich; *Polymerase chain reaction* J Clin Immunol; Nov.1989; 9(6);437-447.

Hea-Jin Shin, et al.; "Cloning, Expression, and Characterization of a Family B-Type DNA Polymerase from the Hyperthermophilic Crenarchaeon *Pyrobaculum arsenaticum* andf Its Application to PCR"; J. Microbiol Biotechnol; (2005); 15(6); pp. 1359-1367.

Mary C. Longo, et al.; "Use of uracil DNA glycosylase to control carry-over contamination in polymerase chain reactions"; Gene 93; (1990); pp. 125-128.

Douglas Hanahan; "Studies on Transformation of *Escherichia coli* with Plasmids"; J. Mol. Biol.; (1983); 166; pp. 557-580.

Sambrook et al.; "*Gel-Filtration Chromatography*" Molecular Cloning: A Laboratory Manual, 2d Ed.; Cold Spring Harbor Laboratory Press (1989).

M. Deutscher; "*Guide to Protein Purification Methods Enzymology*"; vol. 182; Academic Press. Inc., San Diego, CA(1990).

\* cited by examiner

*E. coli* : GQDPYHG — — — — — WGSHAQKK

*Hin* : GQDPYHG — — — — — WGSHAQKK

*Pde* : GQDPYHG — — — — — WGSHAQKK

*Vpa* : GQDPYHG — — — — — WGSHAQKK

BMTU 3346 : GQDPYPT — — — — — WGNDARKN

FIG. 3

SEQUENCE LISTING

<160> NUMBER OF SEQ ID NOS: 28

<210> SEQ ID NO 1
<211> LENGTH: 735
<212> TYPE: DNA
<213> ORGANISM: Psychrobacter sp.

<400> SEQUENCE: 1

```
atggaattat tcgatgaaca aacgccaaaa acgccagcgc aaaaacaagc aattttagac      60
aatgtgcgct tgccagaaga ttggaaaacg gcgttagcag acgagttaac ttctaacaat     120
atggacgact tgcgtgcgtt tttaaaagaa gcctatcaat cagaaaacag tatctatccg     180
ccagcacctt taatatttaa tgcgttaaac ctgaccccct tatcacaaat taaagtcgtg     240
atactagggc aggatccgta tcatggacca gggcaggcaa tgggcttatc gttttcagtg     300
cccaaagtca ttccaaagcc accctcactc aataatttgt taaaagagat ggcaagtgac     360
gttggtatcg caccctcaaa acatggcgac ctgacttact gggcgcagca aggagttttg     420
ctattaaata gctctctgac cgtgcgagaa agtgagccaa atagccatca aaataaaggt     480
tgggagcagt ttaccgatgc ggtgattgat gtggttaatg aacaaacaga acataccgta     540
tttatattgt ggggctctca tgcacaaaaa agcaaatata tcaatactga taagcatctt     600
attctcaccg ctgtacaccc atcaccacta gctgccaatc gtggtggatt ctttggttcc     660
aagccgtttt ctaagaccaa tgattatctg gtacagtatg gcaaacgcc tatcgattgg      720
caattaccgc aatag                                                       735
```

<210> SEQ ID NO 2
<211> LENGTH: 244
<212> TYPE: PRT
<213> ORGANISM: Psychrobacter sp.

<400> SEQUENCE: 2

```
Met Glu Leu Phe Asp Glu Gln Thr Pro Lys Thr Pro Ala Gln Lys Gln
 1               5                  10                  15
Ala Ile Leu Asp Asn Val Arg Leu Pro Glu Asp Trp Lys Thr Ala Leu
            20                  25                  30
Ala Asp Glu Leu Thr Ser Asn Asn Met Asp Asp Leu Arg Ala Phe Leu
        35                  40                  45
Lys Glu Ala Tyr Gln Ser Glu Asn Ser Ile Tyr Pro Pro Ala Pro Leu
    50                  55                  60
Ile Phe Asn Ala Leu Asn Leu Thr Pro Leu Ser Gln Ile Lys Val Val
65                  70                  75                  80
Ile Leu Gly Gln Asp Pro Tyr His Gly Pro Gly Gln Ala Met Gly Leu
                85                  90                  95
Ser Phe Ser Val Pro Lys Val Ile Pro Lys Pro Ser Leu Asn Asn
            100                 105                 110
Leu Leu Lys Glu Met Ala Ser Asp Val Gly Ile Ala Pro Ser Lys His
        115                 120                 125
Gly Asp Leu Thr Tyr Trp Ala Gln Gln Gly Val Leu Leu Leu Asn Ser
    130                 135                 140
Ser Leu Thr Val Arg Glu Ser Glu Pro Asn Ser His Gln Asn Lys Gly
145                 150                 155                 160
Trp Glu Gln Phe Thr Asp Ala Val Ile Asp Val Val Asn Glu Gln Thr
                165                 170                 175
Glu His Thr Val Phe Ile Leu Trp Gly Ser His Ala Gln Lys Ser Lys
            180                 185                 190
Tyr Ile Asn Thr Asp Lys His Leu Ile Leu Thr Ala Val His Pro Ser
        195                 200                 205
Pro Leu Ala Ala Asn Arg Gly Gly Phe Phe Gly Ser Lys Pro Phe Ser
    210                 215                 220
Lys Thr Asn Asp Tyr Leu Val Gln Tyr Gly Gln Thr Pro Ile Asp Trp
```

Gln Leu Pro Gln

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, t, g, unknown or other
<220> FEATURE:
<221> NAME/KEY: modified_base
<222> LOCATION: (12)
<223> OTHER INFORMATION: a, c, t, g, unknown or other

<400> SEQUENCE: 3
ggncargayc cntaycaygg                                            20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: a, c, t, g, unknown or other
<220> FEATURE:
<221> NAME/KEY: modified_base
<222> LOCATION: (15)
<223> OTHER INFORMATION: a, c, t, g, unknown or other
<220> FEATURE:
<221> NAME/KEY: modified_base
<222> LOCATION: (18)
<223> OTHER INFORMATION: a, c, t, g, unknown or other

<400> SEQUENCE: 4
ttyttytgng crtgngmncc cca                                        23

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccattgcct gccctggtc                                             19

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatgtggtta atgaacaaac agaa                                       24

<210> SEQ ID NO 7
<211> LENGTH: 32

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acatcatatg gaattattcg atgaacaaac gc                                    32

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttgactcgag ttgcggtaat tgccaatcga tag                                   33

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aggattacat atggctgcac agcagagcga a                                     31

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ataactcgag ttcagataat ttctttagtt gtctttt                               37

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aataacgtcg gcaactttgg                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttacgccac cagtcatcct                                                  20

<210> SEQ ID NO 13
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 13
caaaggcggt taaggtggta                                                     20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggctgtaccg gacaatgagt                                                     20

<210> SEQ ID NO 15
<211> LENGTH: 7
<212> TYPE: PRT
<213> ORGANISM: Escherichia coli

<400> SEQUENCE: 15

Gly Gln Asp Pro Tyr His Gly
 1               5

<210> SEQ ID NO 16
<211> LENGTH: 8
<212> TYPE: PRT
<213> ORGANISM: Escherichia coli

<400> SEQUENCE: 16

Trp Gly Ser His Ala Gln Lys Lys
 1               5

<210> SEQ ID NO 17
<211> LENGTH: 7
<212> TYPE: PRT
<213> ORGANISM: Haemophilus influenzae

<400> SEQUENCE: 17

Gly Gln Asp Pro Tyr His Gly
 1               5

<210> SEQ ID NO 18
<211> LENGTH: 8
<212> TYPE: PRT
<213> ORGANISM: Haemophilus influenzae

<400> SEQUENCE: 18

Trp Gly Ser His Ala Gln Lys Lys
 1               5

<210> SEQ ID NO 19
<211> LENGTH: 7
<212> TYPE: PRT
<213> ORGANISM: Pseudomonas denitrificans

<400> SEQUENCE: 19

Gly Gln Asp Pro Tyr His Gly
 1               5

<210> SEQ ID NO 20
```

```
<211> LENGTH: 8
<212> TYPE: PRT
<213> ORGANISM: Pseudomonas denitrificans

<400> SEQUENCE: 20

Trp Gly Ser His Ala Gln Lys Lys
 1               5

<210> SEQ ID NO 21
<211> LENGTH: 7
<212> TYPE: PRT
<213> ORGANISM: Vibrio parahaemolyticus

<400> SEQUENCE: 21

Gly Gln Asp Pro Tyr His Gly
 1               5

<210> SEQ ID NO 22
<211> LENGTH: 8
<212> TYPE: PRT
<213> ORGANISM: Vibrio parahaemolyticus

<400> SEQUENCE: 22

Trp Gly Ser His Ala Gln Lys Lys
 1               5

<210> SEQ ID NO 23
<211> LENGTH: 7
<212> TYPE: PRT
<213> ORGANISM: Unknown
<220> FEATURE:
<223> OTHER INFORMATION: Description of Unknown: Marine
      Psychrophile sequence

<400> SEQUENCE: 23

Gly Gln Asp Pro Tyr Pro Thr
 1               5

<210> SEQ ID NO 24
<211> LENGTH: 8
<212> TYPE: PRT
<213> ORGANISM: Unknown
<220> FEATURE:
<223> OTHER INFORMATION: Description of Unknown: Marine
      Psychrophile sequence

<400> SEQUENCE: 24

Trp Gly Asn Asp Ala Arg Lys Met
 1               5

<210> SEQ ID NO 25
<211> LENGTH: 245
<212> TYPE: PRT
<213> ORGANISM: Psychrobacter cryohalolentis

<400> SEQUENCE: 25

Met Glu Leu Phe Asp Val Gln Pro Thr Lys Thr Val Ala Gln Lys Gln
 1               5                  10                  15

Ala Ile Leu Asp Asn Val Arg Leu Pro Glu Asp Trp Lys Gln Ala Leu
             20                  25                  30

Ser Glu Glu Leu Thr Ser Asp Asn Met Asp Ser Leu Arg Ala Phe Leu
         35                  40                  45

Lys Gly Ala Tyr Gln Ser Glu Asp Gly Ile Tyr Pro Pro Ala Gln Leu
     50                  55                  60
```

```
Ile Phe Asn Ala Phe Asn Leu Thr Pro Leu Ser Gln Val Lys Val Val
 65                  70                  75                  80

Ile Leu Gly Gln Asp Pro Tyr His Arg Pro Gly Gln Ala Met Gly Leu
                 85                  90                  95

Ser Phe Ser Val Pro Lys Val Ile Pro Lys Pro Ser Leu Asn Asn
            100                 105                 110

Leu Leu Lys Glu Met Ala Asp Asp Ile Gly Ile Lys Pro Ser Ala His
        115                 120                 125

Gly Asp Leu Thr Tyr Trp Ala Gln Gln Gly Val Leu Leu Leu Asn Ser
    130                 135                 140

Ser Leu Thr Val Arg Glu Gly Glu Pro Asn Ser His Gln Asn Gln Gly
145                 150                 155                 160

Trp Glu Lys Phe Thr Asp Ala Val Ile Asp Val Ile Asn Glu Gln Thr
                165                 170                 175

Glu His Thr Val Phe Ile Leu Trp Gly Ser Lys Ala Gln Lys Lys Gly
            180                 185                 190

Lys Tyr Ile Asn Thr Asp Lys His Leu Ile Leu Thr Ala Val His Pro
        195                 200                 205

Ser Pro Leu Ala Ala Asn Arg Gly Gly Phe Phe Gly Ser Lys Pro Phe
    210                 215                 220

Ser Lys Thr Asn Asp Tyr Leu Val Gln Tyr Gly Gln Thr Pro Ile Asp
225                 230                 235                 240

Trp Gln Leu Pro Gln
                245

<210> SEQ ID NO 26
<211> LENGTH: 237
<212> TYPE: PRT
<213> ORGANISM: Acinetobacter sp.

<400> SEQUENCE: 26

Met Gln Leu Thr Glu Gln His Asp Lys Leu Ser Lys Val Gln Leu
 1               5                  10                  15

Asp Glu Ser Trp Lys His Ser Leu Ala Glu Phe Leu Val Ser Ser Arg
                 20                  25                  30

Met Asp Glu Leu Arg Gln Phe Leu Ile Glu Gln Lys Asn Gln Asp Lys
             35                  40                  45

Val Ile Tyr Pro Pro Ser Lys Gln Ile Phe Asn Ala Leu Asn Thr Thr
         50                  55                  60

Pro Leu Ser Ala Val Lys Val Val Ile Leu Gly Gln Asp Pro Tyr His
 65                  70                  75                  80

Gly Pro Asn Gln Ala Asn Gly Leu Ser Phe Ser Val Gln Lys Gly Ile
                 85                  90                  95

Val Leu Pro Pro Ser Leu Arg Asn Ile Phe His Glu Leu Asn Thr Asp
            100                 105                 110

Leu Gly Ile Pro Val Pro Lys His Gly Asp Leu Thr Lys Trp Ala Asp
        115                 120                 125

Gln Gly Val Leu Leu Leu Asn Ser Val Leu Thr Val Glu Ala Gly Gln
    130                 135                 140

Pro Thr Ser His Gln Lys Arg Gly Trp Glu Gln Phe Thr Asp Ser Ile
145                 150                 155                 160

Ile Asp Val Leu Asn Glu Gln Arg Glu His Val Val Phe Ile Leu Trp
                165                 170                 175

Gly Ala Tyr Ala Gln Arg Lys Gly Gln Arg Ile Asp Arg Glu Lys His
            180                 185                 190
```

Leu Val Leu Lys Ala Ala His Pro Ser Pro Leu Ala Ala Asn Arg Gly
            195                 200                 205

Gly Phe Phe Gly Cys Lys Val Phe Ser Lys Thr Asn Asn Tyr Leu Lys
        210                 215                 220

Gln His Gly Ile Glu Pro Ile Asp Trp Gln Leu Asp Ala
225                 230                 235

<210> SEQ ID NO 27
<211> LENGTH: 230
<212> TYPE: PRT
<213> ORGANISM: Pseudomonas fluorescens

<400> SEQUENCE: 27

Met Thr Ala Asp Asp Arg Ile Lys Leu Glu Pro Ser Trp Lys Glu Ala
1               5                   10                  15

Leu Arg Ala Glu Phe Asp Gln Pro Tyr Met Ser Glu Leu Arg Glu Phe
            20                  25                  30

Leu Arg Gln Glu His Ala Ala Gly Lys Glu Ile Tyr Pro Pro Gly Pro
        35                  40                  45

Met Ile Phe Asn Ala Leu Asn Ser Thr Pro Leu Asp Lys Val Lys Val
    50                  55                  60

Val Ile Leu Gly Gln Asp Pro Tyr His Gly Pro Gly Gln Ala His Gly
65                  70                  75                  80

Leu Cys Phe Ser Val Gln Pro Gly Val Pro Ala Pro Pro Ser Leu Val
                85                  90                  95

Asn Ile Tyr Lys Glu Leu Lys Arg Asp Leu Asn Ile Asp Ile Pro Asn
            100                 105                 110

His Gly Tyr Leu Gln Ser Trp Ala Glu Gln Gly Val Leu Met Leu Asn
        115                 120                 125

Thr Thr Met Thr Val Glu Arg Ala Asn Ala Ala Ser His Ala Gly Lys
    130                 135                 140

Gly Trp Gln Phe Phe Thr Asp Arg Ile Ile Glu Val Val Ser Glu His
145                 150                 155                 160

Gln Pro His Leu Val Phe Leu Leu Trp Gly Ala His Ala Gln Ser Lys
                165                 170                 175

Gln Lys Leu Ile Asp Ala Thr Lys His Leu Val Leu Thr Ser Val His
            180                 185                 190

Pro Ser Pro Leu Ser Ala Tyr Arg Gly Phe Leu Gly Cys Gly His Phe
        195                 200                 205

Ser Arg Thr Asn Lys Tyr Leu Glu Gln Asn Gly Glu Thr Pro Ile Glu
    210                 215                 220

Trp Arg Leu Pro Pro Leu
225                 230

<210> SEQ ID NO 28
<211> LENGTH: 228
<212> TYPE: PRT
<213> ORGANISM: Escherichia coli

<400> SEQUENCE: 28

Ala Asn Glu Leu Thr Trp His Asp Val Leu Ala Glu Glu Lys Gln Gln
1               5                   10                  15

Pro Tyr Phe Leu Asn Thr Leu Gln Thr Val Ala Ser Glu Arg Gln Ser
            20                  25                  30

Gly Val Thr Ile Tyr Pro Pro Gln Lys Asp Val Phe Asn Ala Phe Arg
        35                  40                  45

-continued

```
Phe Thr Glu Leu Gly Asp Val Lys Val Val Ile Leu Gly Gln Asp Pro
         50                  55                  60
Tyr His Gly Pro Gly Gln Ala His Gly Leu Ala Phe Ser Val Arg Pro
 65              70                  75                      80
Gly Ile Ala Ile Pro Pro Ser Leu Leu Asn Met Tyr Lys Glu Leu Glu
                 85                  90                  95
Asn Thr Ile Pro Gly Phe Thr Arg Pro Asn His Gly Tyr Leu Glu Ser
            100             105                 110
Trp Ala Arg Gln Gly Val Leu Leu Leu Asn Thr Val Leu Thr Val Arg
        115             120                 125
Ala Gly Gln Ala His Ser His Ala Ser Leu Gly Trp Glu Thr Phe Thr
    130             135                 140
Asp Lys Val Ile Ser Leu Ile Asn Gln His Arg Glu Gly Val Val Phe
145             150                 155                     160
Leu Leu Trp Gly Ser His Ala Gln Lys Lys Gly Ala Ile Ile Asp Lys
                165                 170                 175
Gln Arg His His Val Leu Lys Ala Pro His Pro Ser Pro Leu Ser Ala
            180                 185                 190
His Arg Gly Phe Phe Gly Cys Asn His Phe Val Leu Ala Asn Gln Trp
        195                 200                 205
Leu Glu Gln Arg Gly Glu Thr Pro Ile Asp Trp Met Pro Val Leu Pro
    210                 215                 220
Ala Glu Ser Glu
225
```

URACIL-DNA GLYCOSYLASE OF *PSYCHROBACTER* SP. HJ147 AND USE THEREOF

CROSS-REFERENCE TO RELATED APPLICATION

The present application claims, under 35 U.S.C. §119, the benefit of Korean Patent Application No. 10-2007-0023976, filed Mar. 12, 2007, the entire contents of which are hereby incorporated by reference.

BACKGROUND

1. Technical Field

The present invention relates to a novel uracil-DNA glycosylase (hereinafter, "UDG"), a polynucleotide encoding the UDG, a recombinant vector comprising the polynucleotide, a host cell transformed by the vector, a method for producing the UDG, and a method for using the same.

2. Background Art

UDG has been known as an enzyme which repairs damaged DNA, by recognizing the damaged moiety of the DNA and hydrolyzing N-glycosylic bond between the deoxyribose sugar and the uracil base in the DNA so as to remove the damaged base from the DNA. UDG has been first isolated from *E. coli*, and then found in various bacteria including *Bacillus*. UDG has a molecular weight of about 25~35 kDa and substrate specificity which specifically and selectively removes uracil bases, among other bases, from DNA [Refer to: Lindahl, T., *Proc. Natl. Acad. Sci. USA* 71, 3649-3653, 1974; Cone, R. et al., *Biochemistry* 16, 3194-3201, 1977].

Uracil is a base normally present in RNA, but sometimes found in DNA. Such presence of uracil in DNA may occur, when uracil generated by naturally-occurring deamination of cytosine is inserted into DNA, or when dUTP, instead of dTTP, is accidentally inserted into DNA during DNA replication process. With regard to this, UDG specifically removes uracil residues present in DNA, not uracil residues in RNA, thus forming an apyrimidinic (AP) site where a base is removed, and facilitating reactions of various DNA-repairing enzymes such as AP endonuclease, DNA polymerase, DNA ligase, or the like. Thereby, processes for repairing damaged or mutated DNA are carried out [See, Chen, R. et al., *J Gen Virol.* 83, 2339-2345, 2002; Lanes, O. et al., *Extremophiles* 6, 73-86, 2002].

Polymerase chain reaction (PCR) is a technique used for isolating or identifying useful genes by amplifying specific nucleic acid regions in large quantities in vitro, with the use of DNA polymerase originated from thermophiles and hyperthermophiles [See: Erlich, H. A., *J Clin Immunol* 9, 437-447, 1989; Shin, H. J. et al., *J Microbiol Biotechnol* 15, 1359-136, 2005]. The PCR technique has contributed to a lowering of the nucleic acid detection limit in a significant way, owing to its increased sensitivity. Currently, this technique is very effectively used for the detection and identification of diseases by detecting viruses and pathogens. However, when the concentration of a nucleic acid is very low, it is still difficult to detect the nucleic acid of interest. Further, it has a problem that the reaction efficiency is different depending on the reaction condition. Still further, one of the most significant problems of this technique in the use of clinical diagnosis is contamination of a sample, which may cause a wrong diagnosis such as false positive. Such contamination can further lead to cross contamination in the process of selecting samples, isolating nucleic acids, transferring the samples, PCR of samples, storing samples and collecting samples from electrophoresis. The sources of contamination during PCR may be cross contamination among samples, DNA contamination in a lab, and carry-over contamination between amplified products and primers of the previous PCR [See: Sobek, H. et al., *FEBS Lett* 388, 1996]. In the case of cross contamination among said contaminations, even if the degree of cross contamination is very small, it causes a problem in that contamination of a sample cannot be recognized with a conventional PCR technique, when it is amplified together with the sample of interest.

Therefore, in recent years, many methods for preventing cross contamination occurring after a PCR process have been developed. In one example of the methods, PCR is carried out by using dUTP instead of dTTP [See, Longo, M. C. et al., *Gene* 93, 125-128, 1990]. Another example of the methods comprises: adding a template DNA and UDG for removing a very small amount of contaminant, uracil-DNA in a sample; heating the mixture to inactivate UDG; adding thereto dUTP instead of dTTP; and carrying out PCR, have been reported. [See: Udaykumar., et al., *Nucleic Acids Res.* 21, 3917-3918, 1993; Taggart et al., *J. Virol. Methods* 105, 57-65, 2002]. In this respect, currently, PCR products which use UDG in the PCR process or contain UDG are commercially available.

However, UDGs originating from *E. coli* mesophiles are not completely inactivated at high temperature over 60° C., but maintain some of their residual activity so that the uracil-containing DNA product which has been amplified in PCR using dUTP undergoes degradation, resulting in reducing the amount of the final product. For example, in a Reverse Transcriptase-PCR (RT-PCR) using dUTP and mesophilic UDG, the first step of an RT-PCR process is conducted generally at a temperature in the range of 55° C. to 60° C. that is a maximum temperature range for the reaction of a reverse transcriptase, in order to unwind the secondary structure of RNA, and this results in significant decrease in the amount of PCR products, due to mesophilic UDG which maintains its residual activity. Therefore, a cumbersome step of inactivating UDG after UDG treatment for removing contaminated dUMP-containing DNA must be conducted, and then PCR with the use of dUTP is carried out.

Recently, development of psychrophilic UDG which is labile to heat, for making it possible to directly carry out PCR or RT-PCR without going through a UDG inactivating step after UDG treatment, has been receiving more attentions. However, there has been just one psychrophilic UDG which becomes easily inactivated by heat, reported so far, which is an enzyme isolated from a marine psychrophilic BMTU3346 [See: Jaeger, S. et al., *Extremophiles* 4, 115-122, 2000].

There is thus a need for a novel UDG which can solve the above-described problems associated with prior art.

The information disclosed in this Background of the Invention section is only for enhancement of understanding of the background of the invention and should not be taken as an acknowledgement or any form of suggestion that this information forms the prior art that is already known to a person skilled in the art.

SUMMARY OF THE INVENTION

One object of the present invention is to provide a heat-labile psychrophilic UDG which makes it possible to directly carry out PCR or RT-PCR without going through an extra step of inactivating UDG with heat, after the use of UDG.

Another object of the present invention is to provide a polynucleotide of the psychrophilic UDG, and a recombinant vector comprising the same.

Yet another object of the present invention is to provide a composition for PCR, which comprises the psychrophilic UDG.

Still another object of the present invention is to provide a method for eliminating cross contamination and carry-over contamination of PCR reaction products by using the composition for PCR.

BRIEF DESCRIPTION OF THE DRAWINGS

FIG. 3 shows multiple sequence alignments in which amino acid sequence of the entire uracil-DNA glycosylase (UDG) gene originated from Psp HJ147 (SEQ ID NO: 2) are compared with those of *Psychrobacter cryohalolentis* K5 UDG (Pcr K5) (SEQ ID NO: 25), *Acinetobacter* sp. ADP1 UDG (Asp ADP1) (SEQ ID NO: 26), *Pseudomonas fluorescens* Pf-5 UDG (Pfl Pf-5) (SEQ ID NO: 27) and *E. coli* UDG (*E. coli*) (SEQ ID NO: 28), respectively.

DETAILED DESCRIPTION

Figures 1, 2:
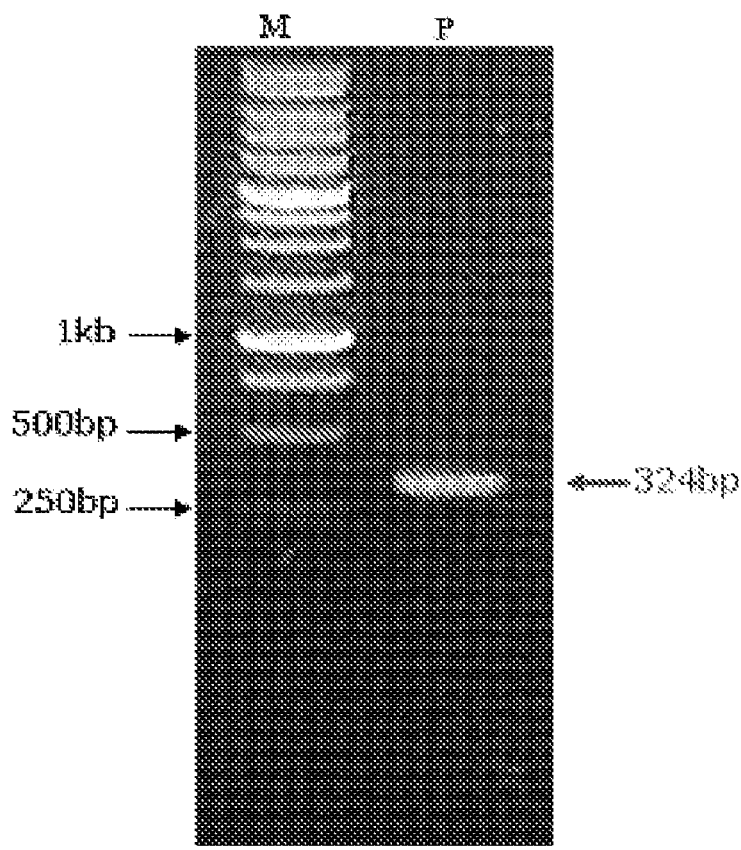
FIG. 1 represents amino acid sequences corresponding to a part of the amino acid sequences commonly conserved in *Escherichia coli* (*E. coli*), (SEQ ID NOS. 15 and 16), *Haemophilus influenzae* (Hin), (SEQ ID NOS 17 and 18), *Pseudomonas denitrificans* (Pde) (SEQ ID NOS 19 and 20), *Vibrio parahaemolyticus* (Vpa) (SEQ ID NOS 21 and 22) and BMTU3346 (SEQ ID NOS 23 and 24) which is a marine psychrophile.
FIG. 2 is a result of an agarose gel electrophoresis of PCR product which is obtained by using genomic DNA of *Psychrobacter* sp. HJ147 as a template and a designed degenerate-primers in PCR (M; 1 kb ladder marker DNA, P; PCR result obtained by using *Psychrobacter* sp. HJ147 (Psp HJ147) strain as a template).

As discussed above, in one aspect, the present invention provides a novel UDG originating from *Psychrobacter* sp. HJ147 strain; a polynucleotide encoding the UDG; a recombinant vector comprising the polynucleotide and a host transformed by the vector.

The present inventors used psychrophiles to discover a novel UDG, since enzymes produced by psychrophiles can manage stable enzymatic reactions at low temperature, while having the same functions as those produced by mesophiles. The present inventors first prepared degenerate primers which bind to the region commonly conserved in conventional UDG genes, and carried out PCR with genomic DNA of a psychrophile *Psychrobacter* sp. HJ147, obtained from the Korea Ocean Research & Development Institute (KORDI), resulting in a DNA product of about 324 bp.

Figure 3:
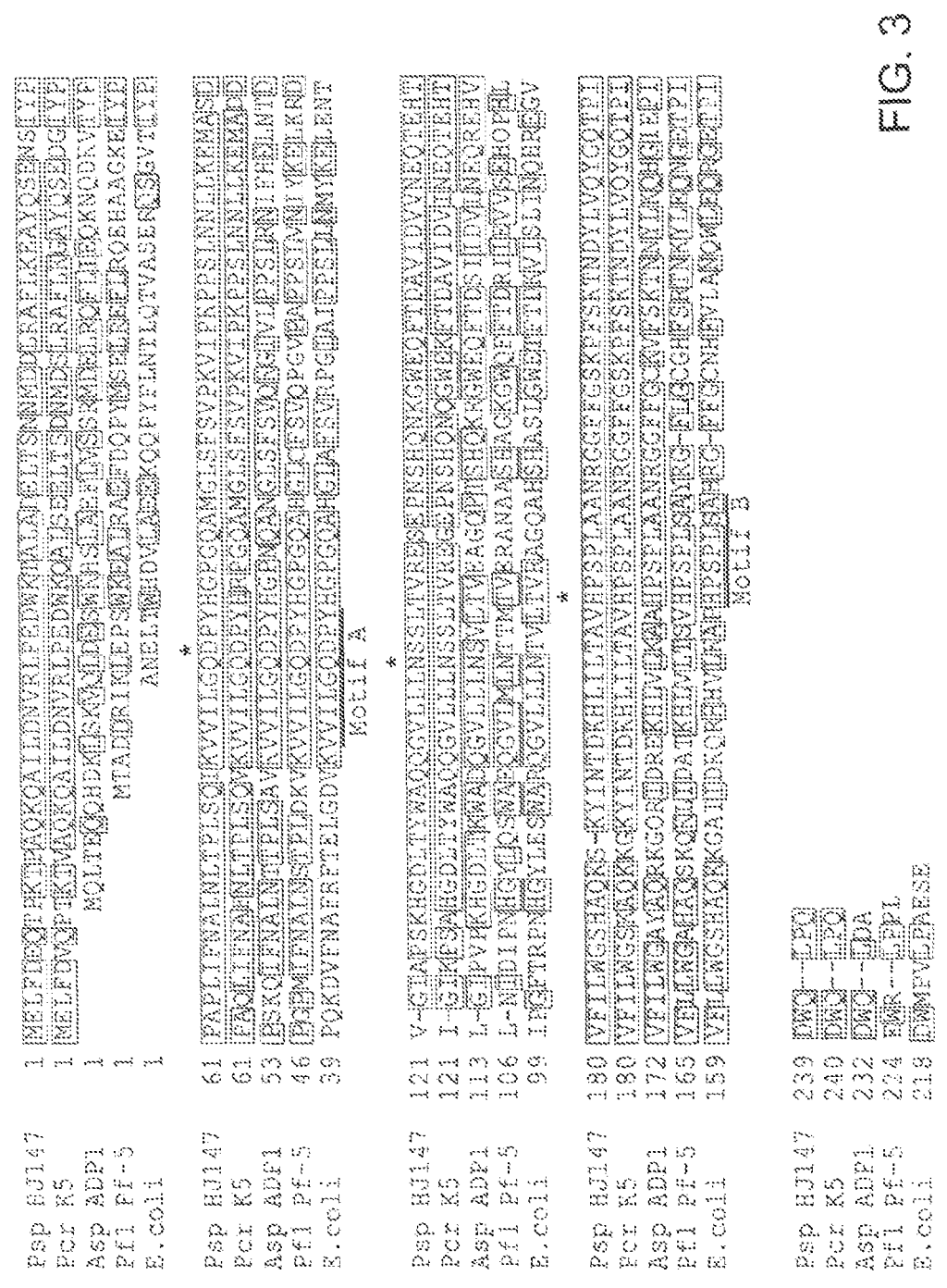

Subsequently, a base sequence of the amplified DNA was analyzed, the result of which showed high sequence homology with the base sequence of reported UDG genes of other species. Then, for obtaining the complete UDG gene from the amplified DNA from *Psychrobacter* sp. HJ147, an inverse PCR method was conducted and the nucleotide sequence of the amplified PCR product was determined. From this, it was found that the entire gene of UDG isolated from *Psychrobacter* sp. HJ147 was comprised of a base sequence of 735 bp in total and 244 amino acids, and the molecular weight of the protein was estimated to be about 27.1 kDa. When compared with other species as shown in FIG. 3, it showed a base sequence homology of 89.3% with *Psychrobacter cryohalolentis* K5; 60.6% with *Acinetobacter* sp. ADP1; 51.2% with *Pseudomonas fluorescens* Pf-5; and 45.4% with *Escherichia coli*. Three of D (Asp), N (Asn) and H (His) are important amino acids involved in UDG activity, and the three amino acids are well-conserved as shown in FIG. 3 [See: Sartori, A. A. et al., *EMBO J.* 21, 3182-3191, 2002]. Particularly, the motif A and motif B regions, each of which includes well-conserved D (ASP) at the $85^{th}$ position and H (His) at the $206^{th}$ position, were identified (See FIG. 3).

In order to find out the activity of UDG expressed from the UDG gene obtained by the above-described method, the present inventors carried out cloning of the UDG gene to a vector being able to express the UDG gene, and the resulting expression vector (pTPSUDG) was transformed into a host cell. Then, the UDG according to the present invention expressed in the transformed host cell was purified through an IMPACT-CN system.

In the meantime, UDGs are known to have an enzymatic activity of removing uracil bases from DNA. In order to confirm that the UDG of the present invention has the same enzymatic activity as mentioned above, UDG activity was measured by using a uracil-containing DNA substrate. The result showed that the UDG of the present invention removed uracil bases from a DNA substrate, confirming the enzymatic activity of UDG.

In addition, optimum pH and temperature for the UDG activity were investigated. The result revealed that the pH value at which enzymatic activity reached its top level was pH 7.0 (See, FIG. 6), and the optimum temperature was 25° C. (See, FIG. 7). It was also found that, at a temperature of 30° C. or higher, the enzymatic activity became rapidly reduced and finally disappeared. From these results, it can be recognized that the UDG of the present invention is characteristically inactivated at a temperature of 50° C. or lower (See, FIG. 8), contrary to the UDG of *E. coli* and other UDGs, both of which maintain their activity even at a temperatures of 60° C. or higher.

Further, heat stability of the UDG of the present invention was investigated. The result showed that heat stability of the UDG rapidly reduced at 50° C., and then the activity was completely lost within 5 minutes (See, FIG. 7). This result corresponds to the test result regarding the investigation of the optimum temperature, confirming again that the UDG of the present invention is easily inactivated at 50° C.

Figure 9:
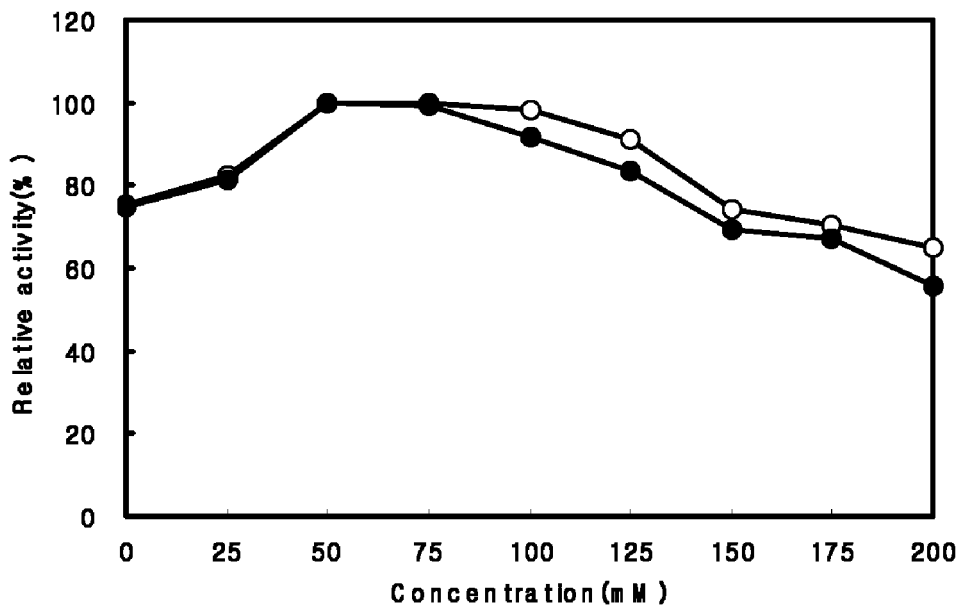
FIG. 9 is a plot showing the relative enzyme activity of UDG according to the present invention as a function of NaCl (●) and KCl (○) concentration.

The enzymatic activity of the UDG of the present invention was further investigated, utilizing NaCl and KCl. It can be seen that the activity is higher at a concentration in the range of 50~75 mM (See. FIG. 9).

Figure 10:
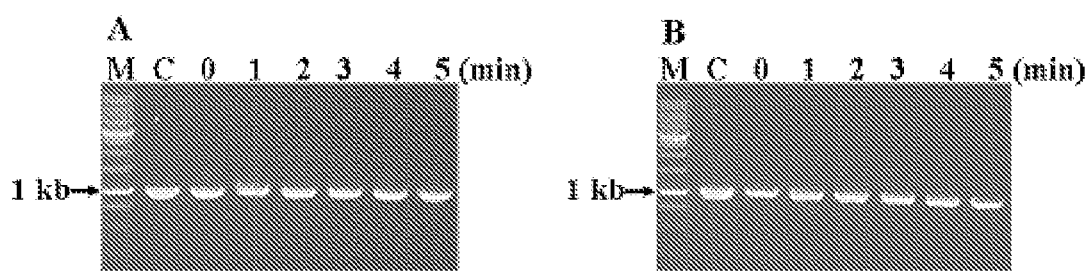
FIG. 10 shows the results of an agarose gel electrophoresis for the digestion of 1 kb DNA substrates amplified by PCR using UDG (A) of the present invention and *E. coli* UDG (B), where the enzyme was digested at 25° C. for the indicated times.
Figure 11:
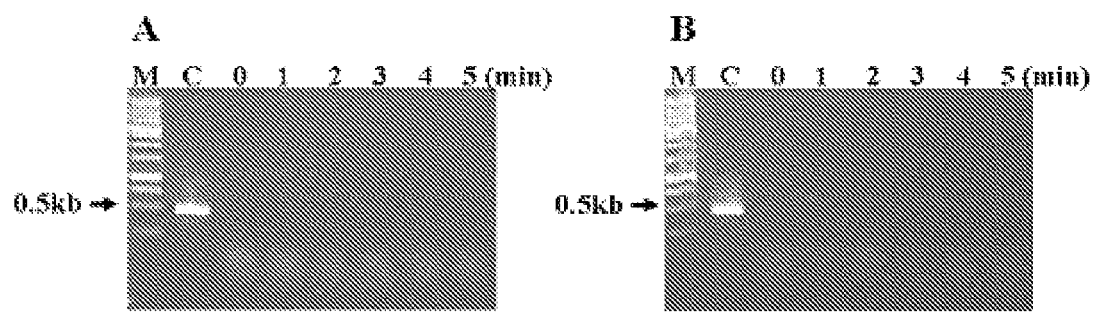
FIG. 11 shows the results of an agarose gel electrophoresis for the digestion of 0.5 kb uracil DNA substrates amplified by PCR using dUTP with UDG (A) of the present invention and *E. coli* UDG (B), where the enzyme was digested at 25° C. for the indicated times.

The present inventors further investigated the substrate specificity and heat stability of the UDG of the present invention, to see whether the UDG is applicable to PCR. First, the substrate specificity of the UDG of the present invention was tested by using substrates comprising dUTP and dTTP, respectively. The result showed that the UDG of the present invention did not work on the substrate comprising dTTP (See, FIG. 10), but efficiently worked on the substrate comprising dUTP (See, FIGS. 11 and 12), just like *E. coli* UDGs and marine psychrophile BMTU. Therefore, it can be recognized that the UDG of the present invention also has substrate specificity to a uracil-containing DNA substrate.

Then, the present inventors applied the UDG of the present invention to PCR. 0.5 kb of a uracil-DNA (contaminated DNA) template and 1 kb of a DNA (normal DNA) template were mixed at a certain concentration to provide a contaminated DNA, and then thereto a PCR mixture comprising the UDG and dUTP was added at once so as to carry out an enzymatic reaction and then PCR. From this, it was found that the PCR reaction product of 0.5 kb uracil-DNA (contaminated DNA) was not amplified, but the PCR product of 1 kb DNA (normal DNA) was amplified (See, FIG. 13). It is thus contemplated that the UDG originating from *Psychrobacter* sp. HJ147 according to the present invention specifically and selectively removes uracil bases from a DNA substrate.

The term "UDG" used with respect to the present invention refers to a polypeptide having an amino acid sequence represented as SEQ ID. NO: 2, including its functional equivalents. The term "functional equivalents" refers to a polypeptide which has substantially the same physiological function as the UDG protein of the present invention, having at least 80%, preferably 90%, of sequence homology with the amino acid sequence of the UDG of the present invention, wherein the difference in the amino acid sequences can result from addition, substitution or deletion of amino acids. "Substantially same physiological function" as used herein, refers to an activity which specifically removes uracil bases from a DNA substrate.

Further, the present invention provides a polynucleotide which encodes the UDG. Preferably, the polynucleotide can be DNA or RNA having a base sequence. The polynucleotide may be obtained from nature or prepared by chemical synthetic methods. However, the polynucleotide may be preferably isolated from psychrophiles, and more preferably isolated from *Psychrobacter* sp. HJ147.

The polynucleotide which encodes the UDG can be inserted into a suitable expression vector. The term "expression vector" refers to a plasmid, virus or other vehicles into which a polynucleotide sequence encoding a UDG protein can be inserted or introduced. The polynucleotide sequence according to the present invention can be operably linked to an expression control sequence. The operably linked gene sequence and expression control sequence can be incorporated into one expression vector that comprises both a selection marker and replication origin. The expression "operably linked" as used herein, means that, when a certain molecule is connected to an expression control sequence, it is connected in a way that the gene expression becomes possible in the linked gene and expression control sequence. "Expression control sequence" as used herein, refers to a DNA sequence which regulates expression of the operably linked polynucleotide sequence in a certain host cell. Such control sequence includes a promoter for conducting transcription, an optional operator sequence for regulating transcription, a sequence coding an mRNA ribosome binding site, and a sequence regulating termination of transcription and translation. Examples of the plasmid may include: *E. coli* plasmids such as pBR322, pBR325, pUC118 and pUC119, pET-22b(+); *Bacillus subtilis* plasmids such as pUB110 and pTP5; and yeast plasmids such as YEp13, YEp24 and YCp50, or the like. As a virus mentioned above, animal viruses such as retrovirus, adenovirus, or vaccinia virus, or insect viruses such as baculovirus may be used. Any suitable vector for introducing a polynucleotide of the present invention into a host cell may be used. However it is preferred to use a vector which has been designed to easily induce protein expression and purify the expressed protein.

In a particular embodiment of the present invention, a recombinant plasmid pTPSUDG for producing UDG of *Psychrobacter* sp. HJ147 was constructed by using expression vector pTYB1 (New England Biolabs, US). By using the resulting pTPSUDG, a transformed *E. coli* strain BL21 (DE3) was obtained (*Escherichia coli* BL21(DE3)/pTPSUDG)), and it was deposited at the Korean Culture Center of Microorganisms (KCCM, located in Seodaemun, Seoul, Korea) on Jan. 23, 2007 with depository number KCCM10838P.

The recombinant vector comprising a polynucleotide of the present invention can be introduced into a host cell through well-known methods in the art. For example, the introduction of a recombinant vector according to the present invention can be conducted by the following non-limiting methods: using $CaCl_2$ and heat shock, particle gun bombardment, Silicon carbide whiskers, sonication, electroporation, PEG (polyethylenglycol) precipitation and the like.

As for the host cell, those skilled in the art will understand that a wide variety of cells may be used to provide the UDG. However, a preferable host cell can be bacteria, for example *E. coli*.

In another aspect, the present invention provides a method for producing the UDG.

The method comprises the steps of: inserting a polynucleotide encoding the UDG into a suitable expression vector; introducing the recombinant vector into a host cell; and culturing the transformed host cell under suitable medium and conditions so as to express the UDG. Methods for expressing a recombinant protein by culturing the transformed cell has been well known in this field. For example, a method may comprise inoculating a transformed cell to a medium suitable for its growth for seed culturing, inoculating the resulting product to a main culture medium, and culturing it under suitable conditions so as to induce protein expression. Then, separation or purification of a UDG protein of the present invention, the expression of which has been induced in the transformed cell, can be carried out by various separation and purification methods well known in this field. For example, after cell lysis and centrifugation of the lysate, salting out (precipitation using ammonium sulfate and sodium phosphate), solvent precipitation (precipitation of a protein fraction with acetone or ethanol), dialysis, gel filtration, ion exchange chromatography, reversed phase column chromatography and affinity chromatography, etc. may be used alone or in combination thereof to produce a UDG protein of the present invention [See: Maniatis et al., Molecular Cloning: A Laboratory Manual, Cold Spring Harbor Laboratory, cold Spring Habor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif.(1990)].

In still another aspect, the present invention provides a composition for PCR, which comprises the UDG.

The composition for PCR may comprise a UDG of the present invention added at a concentration of 0.5~10 units, and reagents conventionally used in the process of amplifying a specific nucleic acid region in large quantities in vitro, wherein said reagents may include various species of polymerases, different types of nucleotide triphosphates (dNTP), primers being capable of amplifying a specific nucleic acid site by binding thereto, suitable buffer solutions, and the like. The polymerases may be DNA polymerase, RNA polymerase or reverse transcriptase separated from a variety of species, and the expression "primers being capable of amplification" refers to a single stranded oligonucleotide that serves as a starting point for template DNA replication under suitable conditions and at a suitable temperature.

The above-mentioned PCR may be any types of PCR known in this field, and may include a direct PCR in which an enzyme UDG, a substrate and a PCR composition are added at once for an enzymatic reaction, and then PCR is practiced, and RT-PCR which utilizes a reverse transcriptase.

In a further aspect, the present invention provides a method for eliminating cross contamination in PCR reaction products. The method comprises a step of reacting a uracil-DNA substrate (contaminant) with a composition for PCR comprising UDG of the present invention at a temperature in the range of 25~50° C. for 0~5 minutes. Since UDG of the present invention specifically removes uracil bases from a DNA substrate, it can characteristically eliminate cross contamination which could occur during a PCR process. The cross contamination refers to contamination which could occur in procedures such as sample selection for PCR, nucleic acid separation, transferring of samples, PCR process of samples, sample storage and recovery of samples, etc. Preferably, the contamination sources may be uracil bases externally added to a DNA substrate, uracil bases naturally inserted into DNA due to naturally-occurring deamination of cytosine, or uracil bases present in the replicated DNA owing to the presence of such naturally inserted uracil bases.

Therefore, the method for eliminating cross contamination in PCR products according to the present invention comprises reacting a uracil-containing DNA substrate with a composition for PCR comprising UDG of the present invention at 25~50° C., in the range of which a UDG protein of the present invention represents enzymatic activity, for 0~5 minutes, and then carrying out PCR by methods well known in this field. Since the UDG protein of the present invention loses its activity during a PCR process which comes after the enzyme reaction and is generally carried out at a temperature in the range of 50~60° C., further degradation or reduction in the resulting PCR products can be prevented.

In one embodiment of the present invention, a uracil base-containing substrate and a composition for PCR comprising a UDG protein of the present invention were reacted at 25° C. for 5 minutes, and PCR was conducted, alternatively PCR was directly conducted without conducting the reaction at 25° C. for 5 minutes. The results demonstrate that a UDG protein of the present invention reduced cross contamination occurring during a PCR process, while having no effect on a PCR process itself.

Hereinafter, the present invention is further illustrated in detail through the following examples. However, the examples are only described with illustrative purposes, and by no means restrict the scope of the present invention.

EXAMPLE 1

Cloning of UDGgene

In search of a novel UDG gene that is active at a low temperature, the present inventors obtained genomic DNA of *Psychrobacter* sp. HJ147 that is a psychrophile taken from the surface of the sea in Hujin harbor, from KORDI. This strain systematically belongs to γ-protobacteria, by using 16S rRNA, and shows a 99% sequence homology with the base sequence of 16S rRNA of *Psychrobacter urativorans* (GenBank No. AJ609555). The genomic DNA of *Psychrobacter* sp. HJ147 obtained from KORDI was used as a template, and primers represented as SEQ ID. NOs: 3 and 4, as shown below, were prepared with reference to the amino acids of well-conserved regions among the conventionally known UDG gene of *Escherichia coli* (*E. coli*), *Haemophilus influenzae* (Hin), *Pseudomonas denitrificans* (Pde), *Vibrio parahaemolyticus* (Vpa) and a marine psychrophile, BMTU3346. With the prepared template and primers, PCR was conducted, using the following temperature profile: initial denaturation at 95° C. for 3 minutes, 5 cycles of 1 minute at 94° C., 1 minute at 53° C. and 1 minute at 68° C.; then 25 cycles of 1 minute at 94° C., 1 minute at 57° C. and 1 minute at 72° C.; and then finally an extension reaction of 10 minutes at 72° C. was done. An amplified product of approximately 324 bp was confirmed by 0.8% agarose gel electrophoresis. The PCR product was purified through 1.5% agarose gel by using a QIAquick Gel Extraction kit (QIAGEN). Then, cloning of the purified product to a vector was carried out by a pGEM-T Easy vector system I (Promega) according to the protocol provided by the manufacturer's instruction. Determination of a base sequence of the cloned DNA was requested to Macrogen Corporation, and the result was compared with base sequences of conventionally known UDGs of other species, which showed a high sequence homology. Therefore, it was confirmed that the cloned 324 bp DNA fragment was a part of UDG gene of *Psychrobacter* sp. HJ147.

```
SEQ ID. NO: 3, primer (P1-1):
5'-GGNCARGAYCCNTAYCAYGG-3'

SEQ ID. NO: 4, primer (P1-2):
5'-TTYTTYTGNGCRTGNGMNCCCCA-3'
```

Here, N may refer to a base of G, A, T or C; R may refer to a base of A or G; Y may refer to a base of C or T; and M may refer to A or C) (See, FIG. 1).

EXAMPLE 2

Cloning of the Entire UDG Gene

Cloning of the entire UDG gene of *Psychrobacter* sp. HJ147 was attempted by using the 324 bp DNA base sequence of UDG of *Psychrobacter* sp. HJ147 obtained from Example 1 as described below. For cloning of the entire UDG gene, an inverse PCR method was employed [See: Ogasawara, N., et al., *DNA Res*, 1, 1-14, 1994]. The inverse PCR is a method for identifying unknown flanking sequences by amplifying the unknown sequences, using an already known sequence.

Firstly, genomic DNA of *Psychrobacter* sp. HJ147 was completely digested with HindIII, and treated with phenol for purification. About 1 μg of the purified DNA fraction was taken, $T_4$ DNA ligase and a reaction buffer solution were added thereto to make the volume 20 μl in total. The resulting mixture underwent self-ligation at 16° C. overnight. For conducting inverse PCR with the ligated DNA product as a template, two internal primers (SEQ ID NOs: 5 and 6) were prepared by using a base sequence of the conserved UDG gene corresponding to about 324 bp that was confirmed with *Psychrobacter* sp. HJ147 of example 1. Using the two internal primers and the ligated DNA product, inverse PCR was conducted with the following temperature profile: initial denaturation at 95° C. for 3 minutes, 30 cycles of 50 seconds at 94° C., 1 minute at 60° C. and 3 minutes at 72° C., and extension of 10 minutes at 72° C. Subsequently, about 828 bp of an amplified DNA fragment was confirmed by 0.8% agarose gel electrophoresis of the resulting product. Determination of a base sequence of the PCR product was requested to Macrogen Corporation. DNA analysis was carried out with the DNAS-TAR program to reveal the entire base sequence of the UDG gene, which was compared with base sequences of UDG genes of *Psychrobacter cryohalolentis* K5, *Acinetobacter* sp. ADP1, *Pseudomonas fluorescens* Pf-5 and *E. coli* by using NCBI BLAST program, regarding base sequence homology.

Internal Primer Sequences

```
SEQ ID. NO: 5, primer (P2-1):
5'-CCCATTGCCTGCCCTGGTC-3'

SEQ ID. NO: 6, primer (P2-2):
5'-GATGTGGTTAATGAACAAACAGAA-3'
```

As a result, the entire base sequence of UDG gene isolated from *Psychrobacter* sp. HJ147 was found to be comprised of 735 bp, including an initiation codon (ATG) and a stop codon (TAG) (See, SEQ ID. NO: 1), and 244 amino acids in total (See, SEQ ID. NO: 2). From the amino acid sequence, the molecular weight of an enzyme UDG of the present invention was estimated to be approximately 27.1 kDa.

Comparing the base sequence of the UDG gene of the present invention isolated from *Psychrobacter* sp. HJ147 (Psp HJ147) with the base sequences of other UDG genes, it showed a sequence homology of 89.3% with UDG of *Psychrobacter cryohalolentis* K5 (Pcr K5), 60.6% with UDG of *Acinetobacter* sp. ADP1 (Asp ADP1), 51.2% with UDG of *Pseudomonas fluorescens* Pf-5 (Pfl Pf-5), and 45.4% with UDG of *E. coli* (See, FIG. 3). Further, it can be found that the three amino acids D (Asp), N (Asn) and H (His), which have been known to be significantly involved in UDG activity, are well conserved as shown in FIG. 3 [See: Sartori, A. A. et al., *EMBO J.* 21, 3182-3191, 2002]. Motif A and Motif B regions, each of which includes particularly well conserved D (ASP) at the $85^{th}$ position and H (His) at the $206^{th}$ position, were confirmed.

EXAMPLE 3

Expression of Recombinant Uracil-DNA Glycosylase (UDG)

Figure 4:
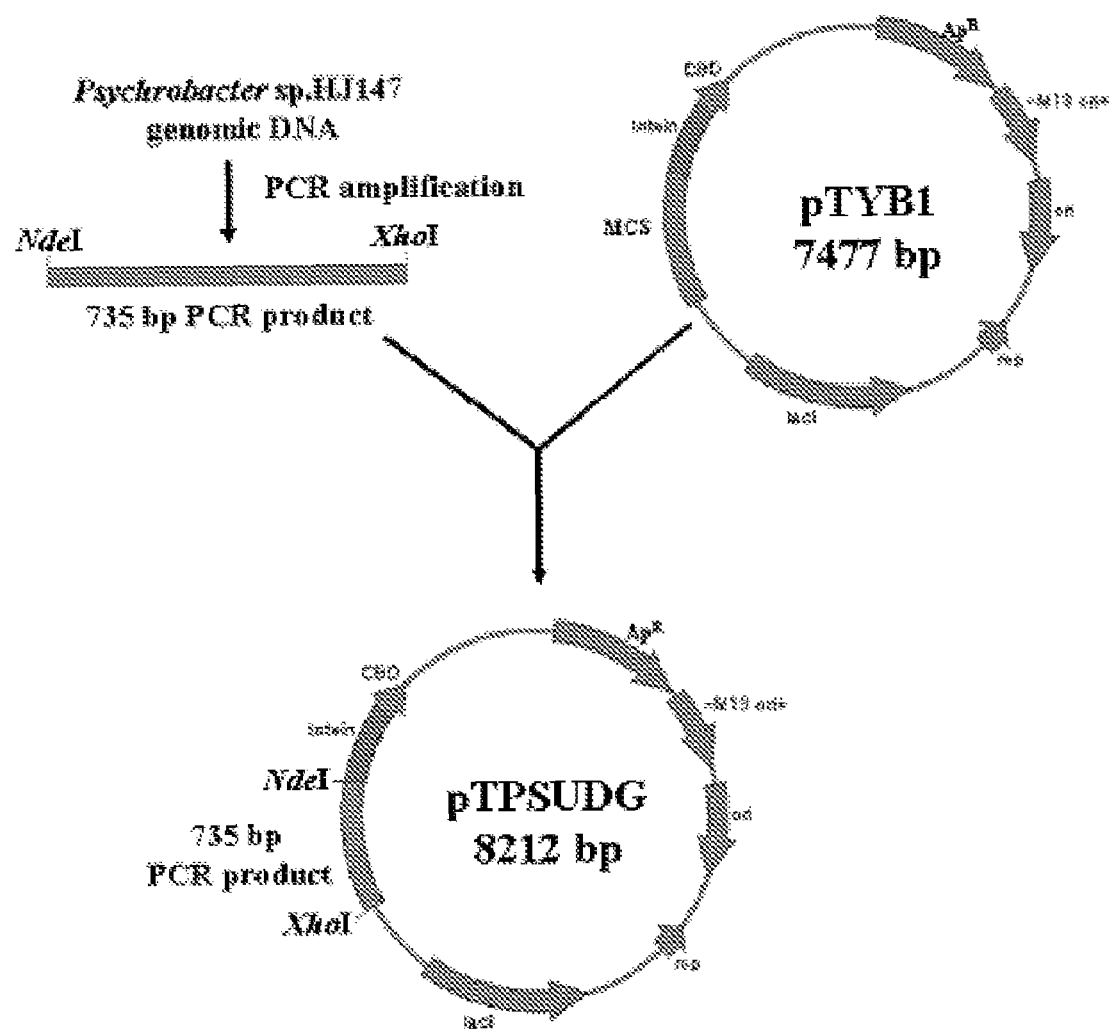
FIG. 4 represents a process for constructing a recombinant plasmid pTPSUDG for the expression of *Psychrobacter* sp. HJ147 UDG.

Genomic DNA of *Psychrobacter* sp. HJ147 was amplified by PCR with the use of primers of SEQ ID. NOs: 7 and 8 which comprise NdeI and XhoI sites artificially inserted thereto to obtain an amplified UDG gene product. The amplified 732 bp fragment (exclusive of a stop codon) of a UDG gene was fractionated on 1.2% agarose gel. The DNA fragment was digested with NdeI and XhoI, and purified. Further, a multiple cloning site (MCS) of an expression vector pTYB1 which has T7 promoter was purified by cutting with NdeI and XhoI. An appropriate amount of pTYB1 vector digested with NdeI and XhoI, and 732 bp of UDG gene digested with NdeI and XhoI were mixed together, and the mixture was allowed for a ligation reaction at 16° C. overnight with $T_4$ DNA ligase so as to construct an expression vector pTPSUDG (See, FIG. 4). For reference, pTYB1 vector (New England Biolabs, US) has 7,477 bp, and is arranged in the following order: T7 promoter, a multiple cloning site (MCS), Sce VMA intein, chitin binding domain (CBD). Therefore, when a UDG gene is inserted to pTYB1 vector and expressed therein, a macromolecule fused with Sce VMA intein and CBD is formed. With a reaction solution comprising pTPSUDG constructed by said ligation, *E. coli* BL21 (DE3) was transformed by Hanahan method [See: Hanahan, D. et al., *J. Mol. Biol.* (1993) 166, 557-580]. Next, the transformed strain was spread over an LB plate where 100 μg/ml of ampicillin was added and cultured at 37° C. overnight. The transformants cultured in the LB plate, to which ampicillin was added, were again serially cultured to a small amount, and plasmid pTPSUDG was isolated therefrom. The isolated plasmid was cut by restriction enzymes NdeI and XhoI, and subjected to 1.2% agarose gel electrophoresis, confirming 732 bp fragment of UDG gene. Thereby, the construction of a normal expression vector pTPSUDG was confirmed. *E. coli* BL21 (DE3) transformed with pTPSUDG as constructed above (*Escherichia coli* BL21 (DE3)/pTPSUDG) was deposited at the KCCM, located in Seodaemun, Seoul, Korea, on January $23^{rd}$, 2007 with depository number KCCM10838P.

```
SEQ ID. NO: 7, primer (P3-1):
5'-ACATCATATGGAATTATTCGATGAACAAACGC-3'
                NdeI SEQ ID. NO: 8, primer (P3-2):
5'-TTGACTCGAGTTGCGGTAATTGCCAATCGATAG-3'
        XhoI
```

EXAMPLE 4

Purification of UDG

In example 4, an enzyme UDG of the present invention is expressed as a fusion protein by using the recombinant strain (*Escherichia coli* BL21 (DE3)/pTPSUDG), which is a transformed *E. coli* by the method of Example 3, and then only UDG of the present invention is cut from the expressed fusion protein and purified, by the following method. *E. coli* BL21

(DE3) comprising the recombinant plasmid of Example 3 was seeded in an LB broth medium comprising 100 μg/ml ampicillin added thereto, cultured at 37° C. overnight, and then 8 ml of the resulting culture was again seeded in 800 ml of the same medium to culture at 37° C. When the optical density at 600 nm reached 0.6, IPTG was added thereto to make the final concentration 0.1 mM, and it was cultured overnight. The resulting product was centrifuged at 6,000 rpm for 15 minutes to collect the *E. coli* cells. The collected cells were suspended in 25 ml sonication buffer (20 mM Tris-HCl (pH 8.0) and 0.5 mM NaCl) which contains 1 mM PMSF, disrupted by sonication, and then centrifuged at 18,000 rpm for 15 minutes to remove cell debris of *E. coli*. All of the procedures described hereafter were conducted at 4° C. as described below, to cut the UDG enzyme from the expressed recombinant fusion protein, as well as to purify only UDG. The supernatant of the crushed cell solution from which precipitates were removed, was loaded to an affinity column IMPACT (Intein Mediated Purification with an Affinity Chitin-binding Tag, BioLabs) so as to bind only the fusion protein to IMPACT column. The column was washed with a column washing buffer [20 mM Tris-HCl (pH 8.0), 500 mM NaCl and 0.1 mM EDTA] having a volume of 10 times greater than that of the column, and was filled with a cleavage buffer, which is a column washing buffer comprising 30 mM DTT added thereto, for cleavage of the fusion protein by intein. After allowing the column to stand over a night, the column was washed with an elution buffer, to which 20 mM Tris-HCl (pH 8.0), 500 mM NaCl and 0.1 mM EDTA were added, so as to separate only the UDG enzyme of the present invention. After collecting the fractions showing UDG activity, it was dialyzed by a buffer solution, to which 20 mM Tris-HCl (pH 8.0) and 50 mM KCl were added.

Figure 5:
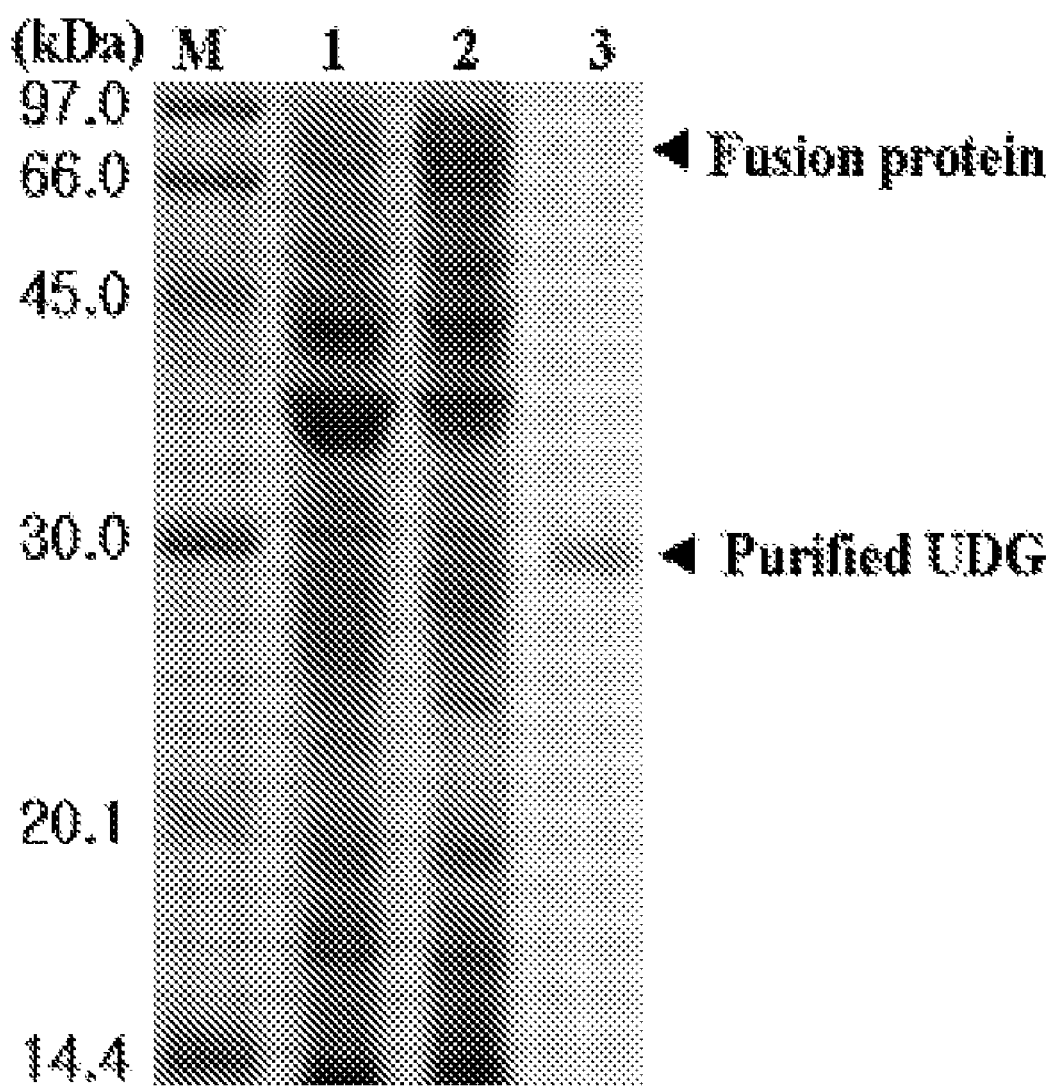
FIG. 5 is an electrophoresis result of a product obtained by expressing a recombinant UDG of the present invention in *E. coli*, and purifying the expressed product by using affinity column (M: marker protein, 1: sonicated extract of uninduced cells, 2: sonicated extract of induced cells, and 3: a fraction purified by IMPACT-CN system).

As a result, *Psychrobacter* sp. HJ147 UDG was purified from the recombinant plasmid pTPSUDG (See, FIG. 5). Lane M in FIG. 5 is a low-molecular-mass markers, and the lane 1 is a transformed recombinant strain, the expression of which was not induced. In lane 2 of FIG. 5, the molecular weight of a fusion protein was expressed to the amount of about 85,000 Da. In lane 3, the molecular weight was found to be about 27,000 Da since a chitin binding protein part was removed by cutting of intein while passing through the IMPACT-CN system, wherein the molecular weight almost corresponded to the calculated molecular weight of the UDG DNA sequence of 27,173 Da. The specific activity of the purified enzyme was 2,768 U/mg.

EXAMPLE 5

Measurement of Activity and Purification Yield of UDG

UDG activity of the present invention was measured by preparing an artificial [³H]-UMP DNA substrate through a PCR technique and using the same, with reference to Lanes' method [See: Secades, P., et al., *FEMS Microbiol*. Lett. 226, 273-279, 2003].

5-1. Preparation of a Substrate by PCR

For measuring the activity of a recombinant UDG enzyme which was purified in Example 4, a uracil-DNA substrate was prepared by PCR of about 1.8 kb of a DNA fragment (*Staphylothermus marinus* DNA ligase gene) as a template and primers (SEQ ID. NOs: 9 and 10) [See: Seo, M. et al., *J. Biotech*. 128, 519-530, 2007]. The PCR mixture (100 μl) was formed by adding: dATP, dCTP, dGTP and dUTP at the final concentration of 0.15 mM, respectively, wherein said dUTP comprises about 2.0 uM of deoxy [5-³H] uridine-5-triphosphate ([³H]-dUTP) (5-30 Ci/mmol, GE Healthcare, code No. TRK351); 700 pg of template DNA; 10 pmol of PCR primer; 5U of super Taq DNA polymerase (RexGene Biotech Co., LTD.); and 10× Super Taq buffer solution II. PCR was conducted by running 30 cycles of 50 seconds at 94° C., 1 minute at 60° C. and 3 and a half minutes at 72° C. From the amplified [³H]-dUTP DNA substrate, unreacted [³H]-dUTP was removed by using a NAP-5 column (Amersham Bioscience). The amount of DNA in the resulting substrate was approximately 65 pg/μl, and the specific activity was about 8,020 cpm/μl.

```
SEQ ID NO: 9, primer (P4-1):
5'-AGGATTACATATGGCTGCACAGCAGAGCGAA-3'

SEQ ID NO: 10, primer (P4-2):
5'-ATAACTCGAGTTCAGATAATTTCTTTAGTTGTCTTTT-3'
```

5-2. Measurement of UDG Activity

For a basic method of measuring activity of UDG of the present invention, 50 mM Tris-HCl (pH 8.5), 50 mM KCl, 1 mM EDTA, 2 ug/ml BSA, 1 mM DTT, 7 μl of [³H]-dUTP DNA substrate (about 455 pg, 56,140 cpm), 1 μl of a UDG enzyme were used to form a solution with the final volume of 20 μl. The mixture was allowed to stand for reaction at 25° C. for 10 minutes, and thereto 20 μl of ice-cold single-stranded calf-thymus DNA (1 mg/ml) and 200 μl of 25% (w/v) trichloroacetic acid (TCA) were added in ice. The resulting mixture was allowed to stand in ice for 15 minutes, and then centrifuged at 13,000 rpm for 20 minutes. 120 μl of the supernatant comprising acid-soluble [³H]-uracil was collected and loaded to a Beckman LS 6800 liquid scintillation counter for measurement. 1 unit of UDG was determined as an amount of enzyme which releases 1 pmol of [³H]-uracil from a substrate at 25° C. for 1 minute.

The total activity of UDG of the present invention obtained by collecting recombinant strains cultured in 800 ml of LB broth, crushing the *E. coli* cells, and cutting of fusion protein and purifying the UDG through IMPACT, was 4,125 U/mg, and the specific activity was 2,768 U/mg.

5-3. Determination of Optimum pH for Activity

In order to determine the optimum pH for the activity of a UDG enzyme of the present invention, the UDG enzyme activity was measured by the same method as described in <5-2>, while modifying the pH condition by 0.5 in the range of 5.5 to 10.0. At this time, 50 mM MES-NaOH buffer solution was used in the pH range of 5.5-6.5; 50 mM Mops-NaOH buffer solution was used in the pH range of 6.5-7.5; and 50 mM Tris-HCl buffer solution was used in the pH range of 7.5-9.0.

Figure 6:
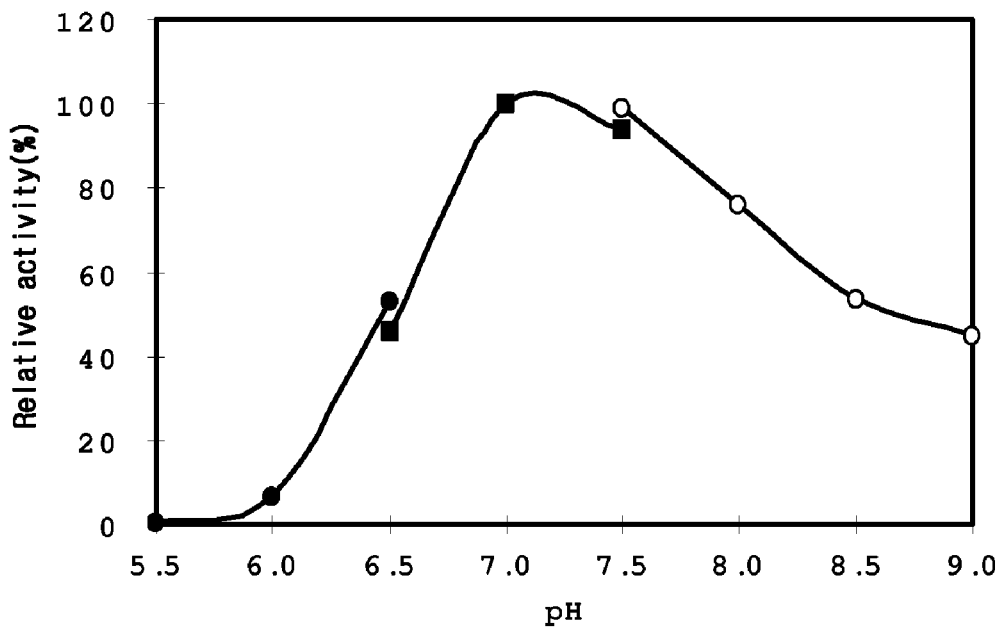
FIG. 6 is a plot showing the relative enzyme activity of UDG according to the present invention as a function of pH.

As a result, it was confirmed that the activity of a UDG enzyme of the present invention was, as shown in FIG. 6, high in the pH range of 7.0-7.5, and thereby the said range is the optimum pH range for the enzyme activity of the present invention. Particularly, enzyme activity reached its peak at a pH value of 7.0 where Mops-NaOH buffer solution was used, and at pH 7.5 where Tris-HCl buffer solution was used. On the contrary, the UDG enzyme activity of the present invention was shown to be rapidly decreased at a pH value of 6.5 or less, or 8.0 or more.

5-4. Determination of Optimum Temperature

In order to determine the optimum temperature condition for the best activity of a UDG enzyme of the present invention, the UDG enzyme activity was measured by the same method as described in the above <5-2>, while varying the reaction temperature by 5-10° C. in the range of 10-80° C.

Figure 7:
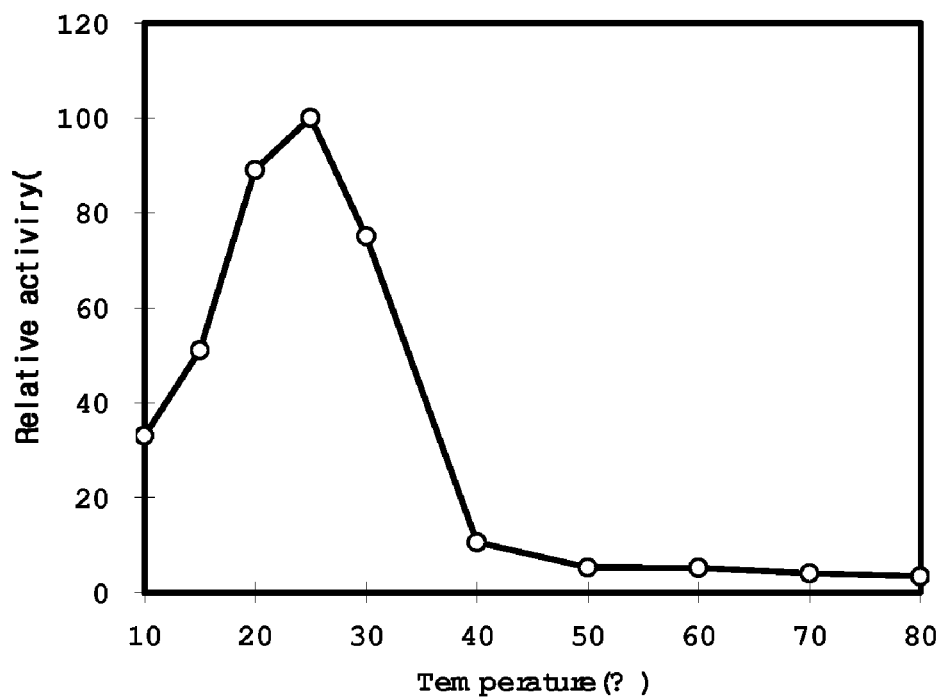
FIG. 7 is a plot showing the relative enzyme activity of UDG according to the present invention as a function of temperature.

As a result, it was confirmed that the optimum temperature for the best UDG enzyme activity of the present invention was 25° C., as shown in FIG. 7. Particularly, it was found that the enzyme activity became rapidly reduced at temperatures higher than 30° C.

5-5. Measurement of Thermostability

In order to determine thermostability of the UDG enzyme of the present invention, the UDG enzyme activity was measured by the same method as described in <5-2> above, while reacting the reaction mixture of <5-2> at each temperature condition of 25° C., 40° C. and 50° C., and taking samples at the time points of 0, 1, 1.5, 2, 2.5, 3, 4, 5 and 10 minutes, 6 hours, 12 hours, and 24 hours.

From the results, it was found that 50% of UDG enzyme activity was maintained at 40° C. for 2 minutes, when UDG of the present invention was reacted at 40° C. (●) and 50° C. (○) for 5~10 minutes, but at 25° C., the activity was maintained fully even after 24 hours (not shown). However, at 50° C., thermostability of the enzyme fell rapidly, and the activity became nearly 0 within a time period of 2 and a half minutes (See, FIG. 8). Therefore, it can be found that a UDG enzyme of the present invention easily loses its activity relatively low temperatures, as compared to the fact that a conventional UDG enzyme of *E. coli* retains its activity even at 60° C. or more.

5-6. Determination of Optimum NaCl and KCl Level

In order to determine the optimum NaCl (●) and KCl (○) level for the best activity of a UDG enzyme of the present invention, the UDG enzyme activity was measured by the same method as described in <5-2> above, while varying the concentrations of NaCl and KCl by the interval of 25 mM within the range of 0-200 mM.

As shown in FIG. 9, it was confirmed that the optimum concentration of NaCl and KCl for the UDG enzyme activity of the present invention was in the range of 50-75 mM.

EXAMPLE 6

Substrate Specificity of UDG Enzyme and Confirmation of its Inactivation at 50° C.

6-1. Preparation of 0.5 kb Uracil-DNA and 1 kb DNA Substrate by PCR

For applying a UDG enzyme of the present invention to PCR, it is necessary to have substrate specificity for selectively breaking uracil-DNA only, and a characteristic of easily losing its activity by heating.

Firstly, two types of substrates, 0.5 kb uracil-DNA (contaminated DNA) substrate and 1 kb DNA (normal DNA) substrate were prepared by using Lambda DNA as a template. For the amplification of 0.5 kb uracil-DNA substrate and 1 kb DNA substrate, primers represented as each SEQ ID. NOs 11, 12, 13 and 14 were synthesized. The PCR conditions for the synthesis of 0.5 kb uracil-DNA substrate were as follows. 100 µl of PCR mixture was formed by adding: DATP, dCTP, dGTP and dUTP, at the final concentration of 0.25 mM, respectively; 100 ng of lambda DNA; 10 pmole of each primer represented as SEQ ID. NOs: 11 and 12; 2.5 U super Taq DNA polymerase; and 10× super Taq buffer solution II. PCR was conducted by running 30 cycles of 50 seconds at 94° C., 1 minute at 58° C. and 2 and a half minute at 72° C. The PCR conditions for the synthesis of 1 kb uracil-DNA substrate were the same as the PCR conditions for the synthesis of 0.5 kb uracil-DNA substrate, except that dTTP was added instead of dUTP, and primers represented as SEQ ID. NOs: 13 and 14 were added, respectively. The two types of substrates were prepared by PCR, and then the resulting PCR products were isolated by using a PCR purification kit for purification and thus separated products were used as each substrate.

① 0.5 kbprimer
SEQ ID. NO: 11, primer (P5-1):
5'-AATAACGTCGGCAACTTTGG-3'
(Lambda genome sequence NO. 14074-14093)

SEQ ID. NO: 12, primer (P5-2):
5'-GTTACGCCACCAGTCATCCT-3'
(Lambda genome sequence NO. 14556-14575)

② 1 kb primer
SEQ ID. NO: 13, primer (P6-1):
5'-CAAAGGCGGTTAAGGTGGTA-3'
(Lambda genome sequence NO. 20791-20810)

SEQ ID. NO: 14, primer (P6-2):
5'-GGCTGTACCGGACAATGAGT-3'
(Lambda genome sequence NO. 21768-21787)

6-2. Effect of UDG Treatment in 1 kb DNA Substrate 0.5 U of the purified UDG enzyme of the present invention and a reaction buffer solution (50 mM Tris-HCl (pH 8.5), 50 mM KCl, 1 mM EDTA, 2 ug/ml BSA, and 1 mM DTT) were mixed with 1 ug of 1 kb DNA substrate to make the final volume of the mixed solution 20 µl. The resulting mixture was subjected to an enzymatic reaction at 25° C. for 1-5 minutes, then heat treatment at 95° C. for 5 minutes for enzyme inactivation, and then confirmed by 1% agarose gel electrophoresis (A in FIG. 10). B in FIG. 10 was also confirmed by the same method, with the use of UDG of *E. coli* which was treated in the same way as in the above-described method. In A of FIG. 10, lane M is 1 kb ladder, and lane C is a control 1 kb DNA which was not treated with UDG. Lanes 0-5 represent results obtained at each reaction period after the addition of UDG. To 1 kb DNA substrate which was prepared by using lambda DNA as a template and amplified by PCR, UDG of the present invention and UDG of *E. coli* were added. Each resulting mixture was treated at 25° C. for varied periods of time. It was found that the DNA substrate was not decomposed at all, by both of the UDGs.

6-3. Effect of UDG Treatment in 0.5 kb Uracil-DNA Substrate 0.5 U of the purified UDG enzyme of the present invention and a reaction buffer solution (50 mM Tris-HCl (pH 8.5), 50 mM KCl, 1 mM EDTA, 2 ug/ml BSA, and 1 mM DTT) were mixed with 1 ug of 0.5 kb uracil-DNA substrate to make the final volume of the mixed solution 20 µl. The resulting mixture was subjected to an enzymatic reaction at 25° C. for 1-5 minutes, then heat treated at 95° C. for 5 minutes for enzyme inactivation, and then confirmed by 1% agarose gel electrophoresis (A in FIG. 11). B in FIG. 11 was also confirmed by the same method, with the use of UDG of *E. coli* which was treated in the same way as in the above-described method. In A of FIG. 11, lane M is 1 kb ladder, and lane C is a control 1 kb DNA which was not treated with UDG. Lanes 0-5 represent results obtained at each reaction period after the addition of UDG. To 0.5 kb uracil-DNA substrate which was amplified by PCR, UDG of the present invention and UDG of *E. coli* were added. Each resulting mixture was treated at 25° C. for varied periods of time. It was found that the uracil-DNA substrate was completely decomposed by both of the UDGs. Therefore, it can be concluded that UDG of the present invention only specifically works on a uracil-DNA substrate.

6-4. Effect of UDG Treatment in 0.5 kb Uracil-DNA Substrate at 50° C.

Figure 8:
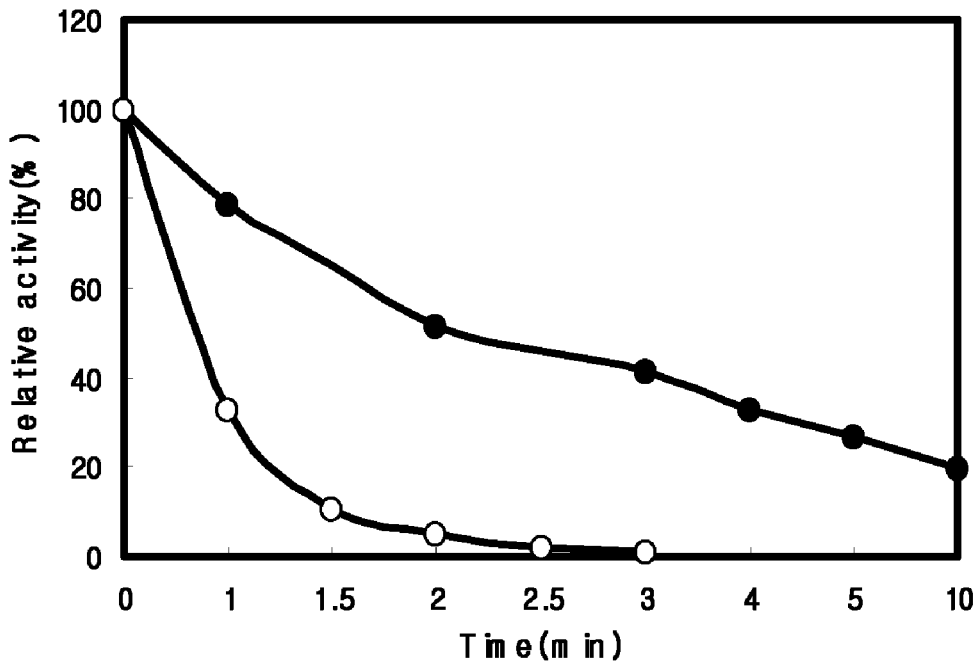
FIG. 8 is a plot showing the relative enzyme activity of UDG according to reaction time at 40° C. (●) and 50° C. (○).
Figure 12:
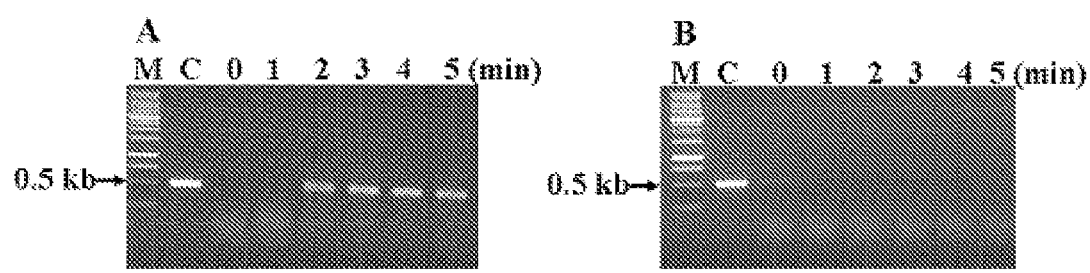
FIG. 12 shows the results of an agarose gel electrophoresis for the digestion of 0.5 kb uracil DNA substrates amplified by PCR using dUTP with UDG (A) of the present invention and *E. coli* UDG (B), where the enzyme was digested at 50° C. for the indicated times.

The purpose of this investigation is to ensure a heat-labile UDG, which makes the application of uracil-DNA glycosylase to PCR easy. To 0.5 kb uracil-DNA amplified by PCR, UDG of the present invention (A of FIG. 12) and UDG of *E. coli* (B of FIG. 12) were added and separately treated at 50° C. for varied periods of time (FIG. 12). From FIG. 12, it can be known that UDG of the present invention can decompose the substrate at 50° C. for 2 minutes, but after 3 minutes, it loses its activity and fails to decompose the substrate (A of FIG. 12). Such result corresponds to the result obtained from an investigation regarding heat resistance of the UDG of the present invention as shown in FIG. 8, wherein the enzyme activity was completely lost within 2 and a half minutes. On the contrary, UDG of *E. coli* was stable even at 50° C., and thus decomposed 0.5 kb uracil-DNA completely (B of FIG. 12). Such result confirmed that the UDG of the present invention got easily inactivated at a relatively lower temperature as compared to UDG of *E. coli*, and accordingly it is possible to use the UDG of the present invention to one-step PCR and RT-PCR.

EXAMPLE 7

Application of UDG of the Present Invention to PCR

By using the UDG of the present invention, it is confirmed whether it is possible to selectively amplify the targeted 1 kb DNA in a mixed substrate that is artificially contaminated uracil-DNA by using 0.5 kb uracil-DNA (contaminated DNA) from Example 7 and 1 kb DNA (normal DNA).

Firstly, an indirect PCR method was carried out, wherein PCR was conducted after adding 0.5 U of UDG to a mixed PCR solution and incubating it at 25° C. for 5 minutes for removing contaminated uracil-DNA from the mixed PCR solution. A direct PCR method was also carried out, wherein PCR was directly conducted without an incubation step at 25° C. The mixed PCR solution was comprised of: 100 ng of substrate which was prepared by mixing 0.5 kb uracil-DNA substrate and 1 kb DNA substrate as prepared above, at a ratio of 1:1; 0.5 U of UDG; 1 U of super Taq DNA polymerase; 0.25 mM dATP, dCTP, dGTP and dUTP; 5 pmole of primer; and 10× super Taq buffer solution II. The PCR mixture was applied to an indirect PCR or a direct PCR method. PCR was conducted by running 20 cycles of 50 seconds at 94° C., 1 minute at 58° C. and 1 and a half minute at 72° C. The PCR reaction products were confirmed by 1% agarose gel electrophoresis.

After adding UDG of the present invention and UDG of *E. coli* at a concentration of 0.5 U, respectively, an indirect PCR in which PCR is conducted after incubation at 25° C. for 5 minutes, was carried out, and then 1% agarose gel electrophoresis was conducted. As a result, it was found that the contaminated 0.5 kb uracil-DNA band had disappeared, and normal 1 kb DNA band was only amplified (A of FIG. 13). From this result, it can be recognized that the UDG worked at a lower temperature so that the contaminated uracil-DNA was surely removed. However, it can be found that, regarding the amplification efficiency of normal 1 kb DNA in PCR, UDG of the present invention was much higher than UDG of *E. coli* (A of FIG. 13). The result of measuring the electrophoresesed agarose gel by using Labwork 4.6 (densitometer) confirmed that UDG of the present invention was 5 times more easily amplifiable than UDG of *E. coli*.

Figure 13:
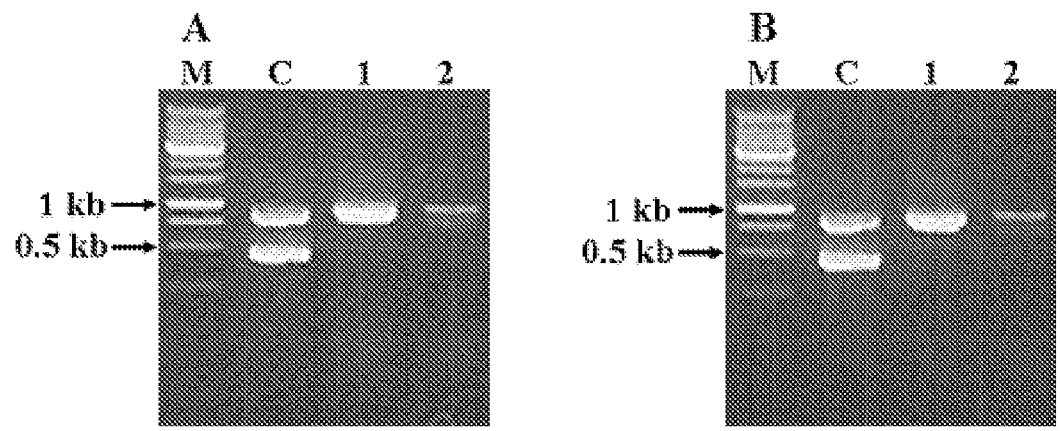
FIG. 13 shows agarose gel electrophoresis results of (A) and (B), wherein (A) is obtained by adding UDG of the present invention and UDG of *E. coli* to an artificially contaminated templates containing 1 kb DNA and 0.5 kb uracil-DNA, and subjecting the resulting mixture to an enzymatic reaction at 25° C. for 5 minutes and subsequently to PCR, and (B) is a result obtained by the same method for (A), except eliminating the enzymatic reaction at 25° C. and carrying out PCR directly (M: 1 kb marker DNA, C: a control without UDG addition, 1: one containing added UDG of the present invention, 2: one containing added UDG of *E. coli*).

When conducting electrophoresis of the direct PCR, in which incubation at 25° C. was eliminated and PCR was carried out directly, by using contaminated DNA with uracil-DNA as a template, only 1 kb DNA band appeared and the band of the contaminated 0.5 kb uracil-DNA did not appear at all (B of FIG. 13). This means that UDG enzyme worked on the PCR reaction mixture while it was being mixed at 4° C. in ice. Regarding the amplification efficiency of normal 1 kb DNA in PCR, it can be found that UDG of the present invention is significantly higher than UDG of *E. coli* (B of FIG. 13). Such result corresponded to the result obtained from said indirect PCR.

This may be explained by higher heat resistance of UDG of *E. coli* as compared to that of UDG of the present invention. Since uracil-containing PCR reaction products are decomposed during the early stage of a PCR process, it is considered that the difference in PCR reaction products becomes greater with the increase of the PCR cycle number.

When UDG of the present invention is used in a PCR process employing dUTP instead of dTTP, it is possible to obtain a precise result without cross contamination and carry-over contamination of uracil-DNA. Therefore, said UDG of the present invention is considered to be a suitable enzyme for clinical diagnosis use.

As described above, a novel UDG of the present invention is an enzyme isolated from a psychrophile, *Psychrobacter* sp. HJ147, which has an activity of removing uracil bases from a uracil-containing DNA substrate and a characteristic of being easily inactivated at low temperature. Since it can eliminate cross contamination and carry-over contamination which could occur in a PCR process, it can be effectively applied to a PCR using dUTP which is widely used in various fields such as experiments in genetic engineering and molecular biology, determination of viral and cancer genes at early stage, diagnosis of hereditary diseases and forensic medicine, for improving preciseness (elimination of false positives), purity and amplification rate of PCR.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. An isolated uracil-DNA glycosylase (UDG) which comprises the amino acid sequence set forth in SEQ ID NO: 2.

2. A composition for PCR, which comprises the uracil-DNA glycosylase according to claim 1.

3. The composition of claim 2, which comprises 0.5-10 units of the uracil-DNA glycosylase of claim 1.

4. The composition of claim 2, which further comprises a polymerase, at least one nucleotide triphosphate, a primer and a buffer.

5. A method for removing cross contamination from PCR reaction products, comprising the steps of:
   (a) reacting a uracil-containing DNA substrate with a composition comprising the uracil-DNA glycosylase according to claim 1 at 50° C. or lower; and
   (b) conducting PCR reaction.

6. The method of claim 5, wherein the step (a) is conducted at 25-50° C. for 0-5 minutes.

* * * * *